(12) United States Patent
Adl

(10) Patent No.: US 8,357,200 B2
(45) Date of Patent: Jan. 22, 2013

(54) HINGED ARTIFICIAL SPINAL DISK DEVICE

(76) Inventor: Ali Adl, Freehold, NJ (US)

( * ) Notice: Subject to any disclaimer, the term of this patent is extended or adjusted under 35 U.S.C. 154(b) by 1332 days.

(21) Appl. No.: 11/911,661

(22) PCT Filed: Apr. 18, 2006

(86) PCT No.: PCT/US2006/014755
§ 371 (c)(1),
(2), (4) Date: Oct. 15, 2007

(87) PCT Pub. No.: WO2006/113812
PCT Pub. Date: Oct. 26, 2006

(65) Prior Publication Data
US 2008/0183294 A1   Jul. 31, 2008

Related U.S. Application Data

(60) Provisional application No. 60/672,612, filed on Apr. 19, 2005.

(51) Int. Cl.
*A61F 2/44* (2006.01)
(52) U.S. Cl. ................... 623/17.14; 623/17.16
(58) Field of Classification Search ..... 623/17.11–17.16
See application file for complete search history.

(56) References Cited

U.S. PATENT DOCUMENTS

| | | | |
|---|---|---|---|
| 4,599,086 A | 7/1986 | Doty | |
| 5,755,796 A * | 5/1998 | Ibo et al. | 623/17.16 |
| 6,106,557 A * | 8/2000 | Robioneck et al. | 623/17.15 |
| 6,120,503 A * | 9/2000 | Michelson | 606/86 A |
| 6,190,388 B1 | 2/2001 | Michelson et al. | |
| 6,432,140 B1 | 8/2002 | Lin | |
| 6,682,561 B2 * | 1/2004 | Songer et al. | 623/17.11 |
| 6,733,531 B1 | 5/2004 | Trieu | |
| 6,805,714 B2 | 10/2004 | Sutcliffe | |
| 6,846,326 B2 | 1/2005 | Zadno-Azizi et al. | |
| 7,060,099 B2 * | 6/2006 | Carli et al. | 623/17.14 |
| 7,172,627 B2 * | 2/2007 | Fiere et al. | 623/17.11 |
| 7,338,525 B2 * | 3/2008 | Ferree | 623/17.11 |
| 7,338,527 B2 * | 3/2008 | Blatt et al. | 623/17.15 |
| 7,628,816 B2 * | 12/2009 | Magerl et al. | 623/17.16 |
| 7,708,760 B2 * | 5/2010 | Parsons | 606/247 |
| 2003/0204260 A1 * | 10/2003 | Ferree | 623/17.11 |
| 2004/0034421 A1 * | 2/2004 | Errico et al. | 623/17.11 |
| 2004/0068321 A1 * | 4/2004 | Ferree | 623/17.16 |
| 2004/0127903 A1 * | 7/2004 | Schlapfer et al. | 606/69 |
| 2004/0143334 A1 | 7/2004 | Ferree | |
| 2005/0033432 A1 * | 2/2005 | Gordon et al. | 623/17.11 |
| 2005/0055095 A1 * | 3/2005 | Errico et al. | 623/17.11 |
| 2005/0101960 A1 * | 5/2005 | Fiere et al. | 606/72 |
| 2005/0159813 A1 * | 7/2005 | Molz, IV | 623/17.11 |
| 2005/0256578 A1 * | 11/2005 | Blatt et al. | 623/17.15 |
| 2006/0235518 A1 * | 10/2006 | Blain | 623/17.11 |
| 2007/0276490 A1 * | 11/2007 | Mateyka | 623/17.11 |

FOREIGN PATENT DOCUMENTS

WO   WO 02080819 A1 * 10/2002
WO   WO 03/005939 A2   1/2003

* cited by examiner

*Primary Examiner* — Eduardo C Robert
*Assistant Examiner* — Lynnsy Schneider
(74) *Attorney, Agent, or Firm* — Hayes Soloway P.C.

(57) ABSTRACT

An artificial spinal disk prosthesis comprised of an artificial disk (101), mounting bracket (105) assembly that secures the disk to at least one vertebrae and a sliding rod (104) that connects the two whereby the shape of the components determines the range of motion of the disk, thus allowing desirable motions of the disk consistent with normal body motions and preventing undesirable motions of the artificial disk. In the preferred embodiment, the angular motion of the disk is controlled by a hinge that is on the side of the artificial disk. In the preferred embodiment, the artificial disc is connected to the spine via one vertebra.

29 Claims, 5 Drawing Sheets

HINGED ARTIFICIAL SPINAL DISK DEVICE

REFERENCE TO RELATED APPLICATION

This application claims priority from U.S. Provisional Patent Application Ser. No. 60/672,612 filed Apr. 19, 2005, the entire content of which is incorporated herein by reference.

BACKGROUND AND SUMMARY OF THE INVENTION

The invention is a minimally invasive total disc replacement device designed with complimentary easy-to-use insertion and removal instrumentation. The invention offers the surgeon the ability to address Lumbar, thoracic and cervical spinal disc disorders. The invention was designed to allow for either full or partial motion rehabilitation as well as a very quick recovery time. It is secured in place by mechanical means and does not require bone to disc fusion, therefore the success of the operation can be readily determined soon after surgery. It is also self-adjusting and as such, a precise placement and positioning is not required. The design allows for a simple disc removal if needed. Most importantly, the design provides for free movement of the artificial disk within carefully controlled ranges of motion and without extraneous penetration of tissue peripheral to its range of operation.

Spinal Disc Orthopaedics

A natural spinal disc accommodates movement freedom for the body it supports. It allows for bending and flexing, for leaning left and right and for rotating. It also supports varying applied loads associated with human body weight and motions.

When the disc gets damaged, a solution needs to be found that mimics the spine in its natural behavior. It needs to accommodate the movement and the applied loads. In some cases (e.g. trauma) there is a benefit in limiting some of the degrees of freedom. As important to the patient, is the requirement that the solution is done using a minimally invasive procedure for implantation. This allows for a quick patient recovery in a matter of days rather than what existing technologies provide. Lastly, the procedure needs to be reversible to allow for unforeseen circumstances and to further lower any risk. The current technologies and procedures can be divided into three categories: Disc repair, disk fusion and disc replacement.

a. Disc Repair:

The procedure calls for surgically removing the fragments of the ruptured disc or removing the herniated part of the disc, which pushes against the nerves causing paralyzing pain and leaving the so called "healthy" part of the disc in place. Although the procedure has advanced greatly and is being performed by microsurgery, allowing relatively quick recovery time, it still has its old problems such as reoccurring herniated or fragmented disc associated with need for repeated surgery, disc thickness reduction and eventually adjacent vertebrae touching each other leading to undesirable permanent disc fusion. In time, the problem often migrates to adjacent discs.

b. Disc Fusion:

The established solution to disc problem is to fuse the upper and lower vertebrae and in most cases adjacent vertebrae by means of mechanical brackets and screws. Some of the problems associated with this approach are: (i) loss of natural body motion, (ii) surrounding organs such as muscles may be permanently damaged and may cause lasting pain for the patient and (iii) very long recovery time. An alternate solution is to apply a spring in a sleeve connector on the outside of the affected vertebrae to allow for some movement. This solution still suffers from drawbacks similar to regular fusion.

c. Artificial Disc Replacement:

The new trend in technology is to replace the disc with an artificial disc, which has two metallic sides with spikes or keels imbedded in the vertebra. That metallic face of the disc touches the adjacent vertebra and promotes bone growth into the metallic disc hence securing it in place. Some of the problems with this approach are:

An approximately two years wait for the bone to grow into the metallic disc and only at that time the success or failure of the operation can be determined. In the case of a successful operation, the fused disc cannot be easily removed if needed. Operation success rate is only about 80%, which is not an acceptable rate for medical implants. A very precise disc placement during the operation is required. Extensive surgeon training is required, which is a considerable drawback for the medical society.

There have been attempts to mitigate these problems by the design of specialized devices. In U.S. Pat. No. 4,599,086 to Doty, a device is disclosed where fixed pins hold the prosthetic vertabrae in a fixed position relative to the neighboring vertebrae. The pins are shown entering the faces of the vertebrae. This design limits movement and, as contrasted with the invention disclosed here, requires more extensive surgical procedures in order to install it. The invention at hand does not require pins on the faces of the vertebrae and in fact is designed to permit the natural movement of the spine. U.S. Pat. No. 6,190,388 to Michelson discloses prosthetic fusion devices that are inserted between the vertebrae whereby the devices are fixed in position by an attachment member. In that patent, a spinal rod is used to hold the fusion devices in place. In this design, motion is limited by the spinal rod and the intent is to promote fusion of the vertebrae—which permanently fixes their position relative to each other. The invention at hand is designed to maintain the motion of the vertebrae by positioning the prosthetic disk using a movable hinging system where multi-dimensional motion is permitted within fixed limits defined by the dimensions of the components. U.S. Pat. App. No. 10754042, by Ferree discloses an artificial disk whose position is maintained between the vertebrae by two metal annulus components that are attached to the opposing faces of the vertebrae. In addition, a cable device is used to assist in the positioning of the disk. This approach also requires extensive surgical interaction because the opposing faces of the vertebrae must be accessed in order to implant the two metal annulus components. In addition, the position of the disk is only limited by the protrusions from the annulus, thus introducing a design trade-off between the danger of the disk falling out of place against the likelihood that the protrusions will be too long thus impacting the neighboring tissue.

U.S. Pat. No. 6,805,714 to Sutcliffe discloses a spinal implant designed to fix the neighboring vertebrae in cases where one of the vertebrae themselves are damaged. This device is designed to fix the position of the vertebrae and promote spinal fusion. This implant design also requires extensive surgical interaction in order that the plates be installed on the opposing faces of the neighboring vertebrae. U.S. Pat. No. 6,846,326 to Cauthen discloses a prosthesis to replace the disk that is comprised of two plates that attach to the opposing faces of the neighboring vertebrae, respectively, using bone fusion. Where the two plates meet, an articulation means permits rocking and twisting motion. This design requires that the vertebrae be fixed during the period that bone fusion with the plates occurs. In addition, the design involves complete removal of the natural tissue in the area.

In U.S. Pat. Application Publication No. 2003/0204260, to Ferree, the description shows an artificial disk prosthesis that is connected by a rigid link to a mounting plate. This design shows that the link member, when moving back and forth with a piston action, extends out from the plate into the surrounding tissue, causing damage and possibly pain. The link member is shown as an integral part of the disk, that is, the rod is fixedly attached to the disk. The design also shows that angulation motion can occur as a result of the link member hinging within a vertical slot. With this approach, the amount of angulation is difficult to control: the geometry requires both tiny machining tolerances to have a properly limited motion while at the same time the backing plate has to be thick enough that the angular stress of the link does not twist it. Ferree also discloses using a swivel to attach the disk to the link, with a vertical pin permitting angulation in the horizontal plane by both the link member and also by the disk. This approach increases the angular range of motion but with no means to accurately control it. This increases the risk that the artificial disk will fall out of place necessitating further surgery. In addition, this approach fixes the link to the disk along the longitudinal axis of the link, which necessitates the link protruding out of the back of the backing plate when the disk moves toward it.

DETAILED DESCRIPTION OF THE PREFERRED EMBODIMENTS

Figure 1:
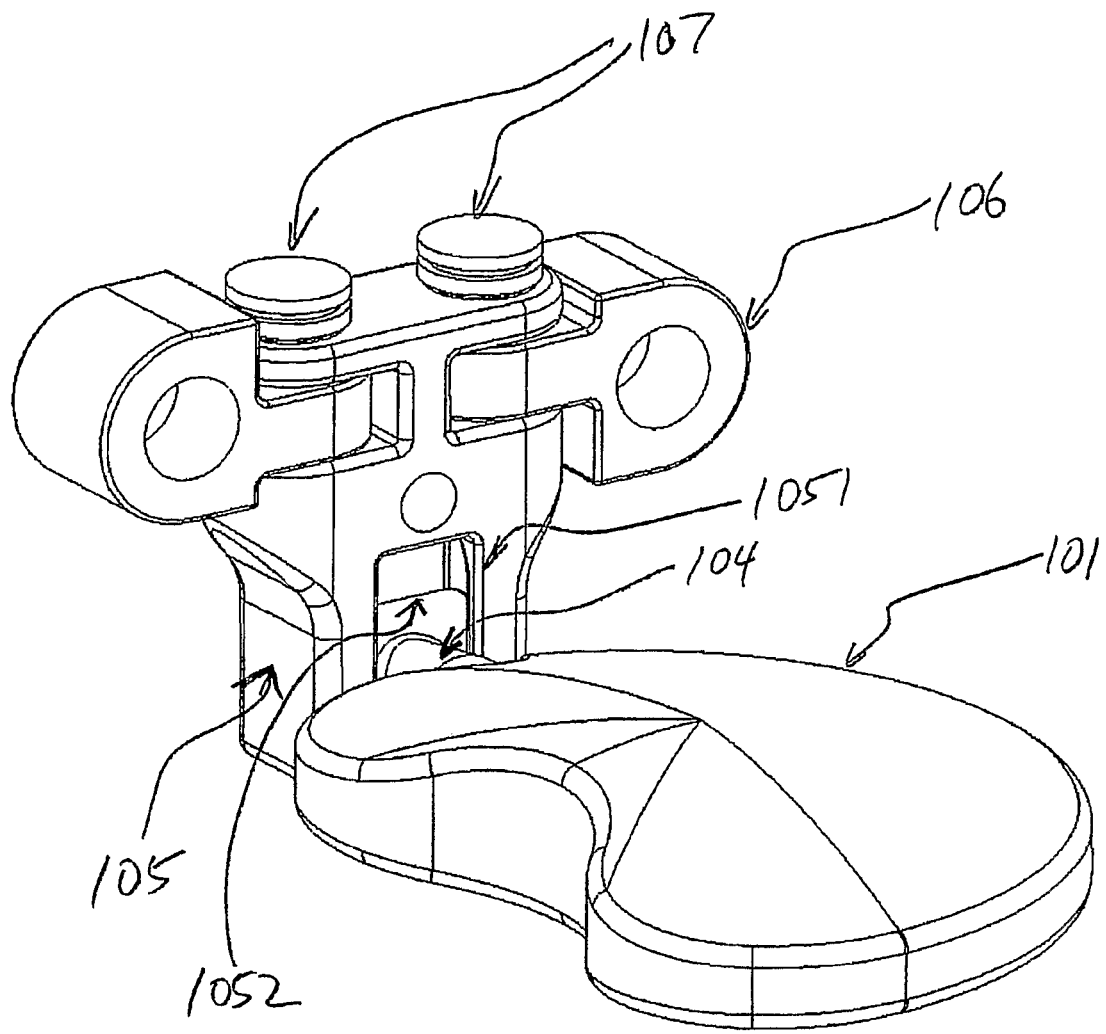
FIG. 1. Shows a top view of the invention.
Figure 2:
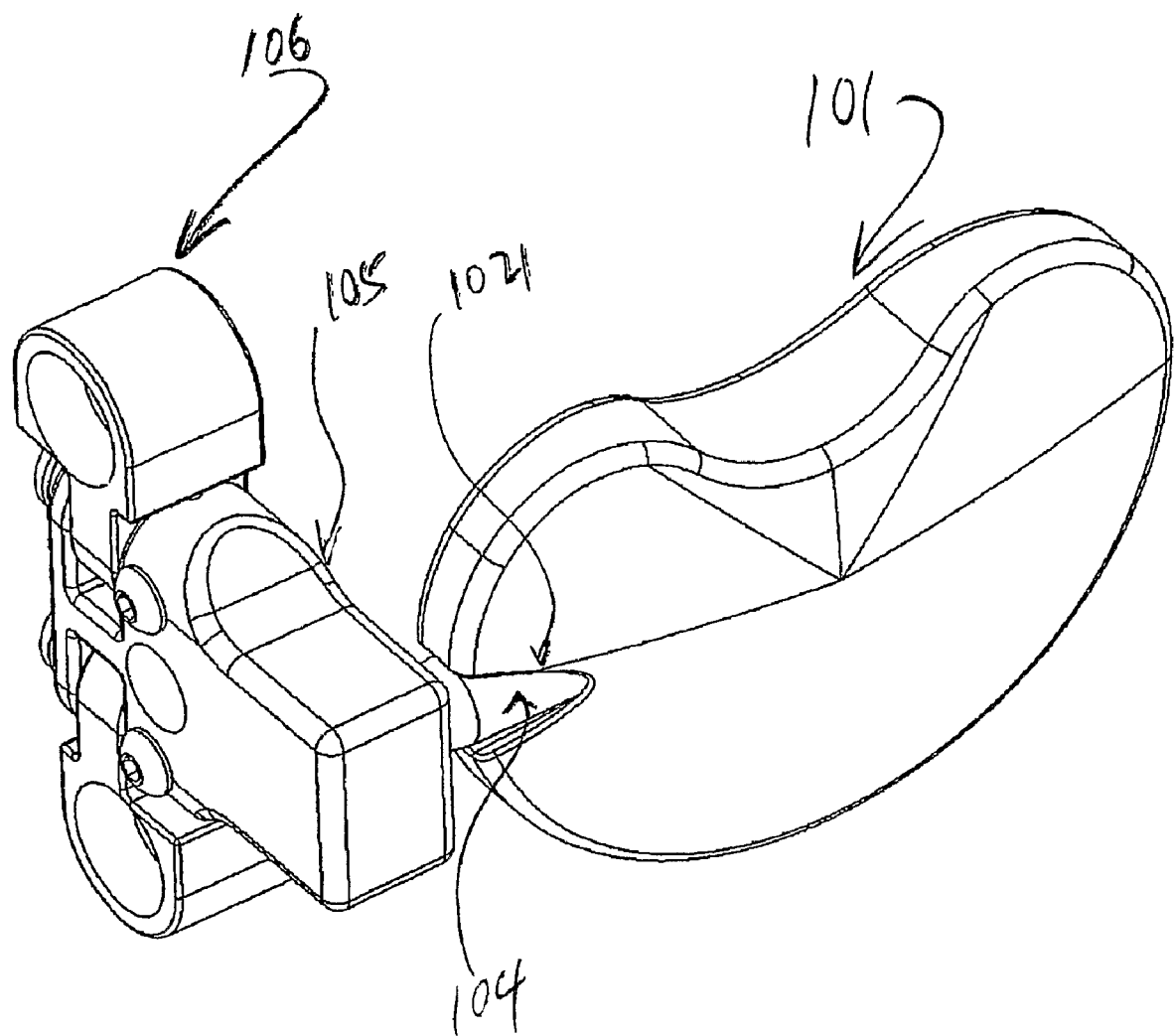
FIG. 2. Shows the bottom view of the invention.
Figure 3:
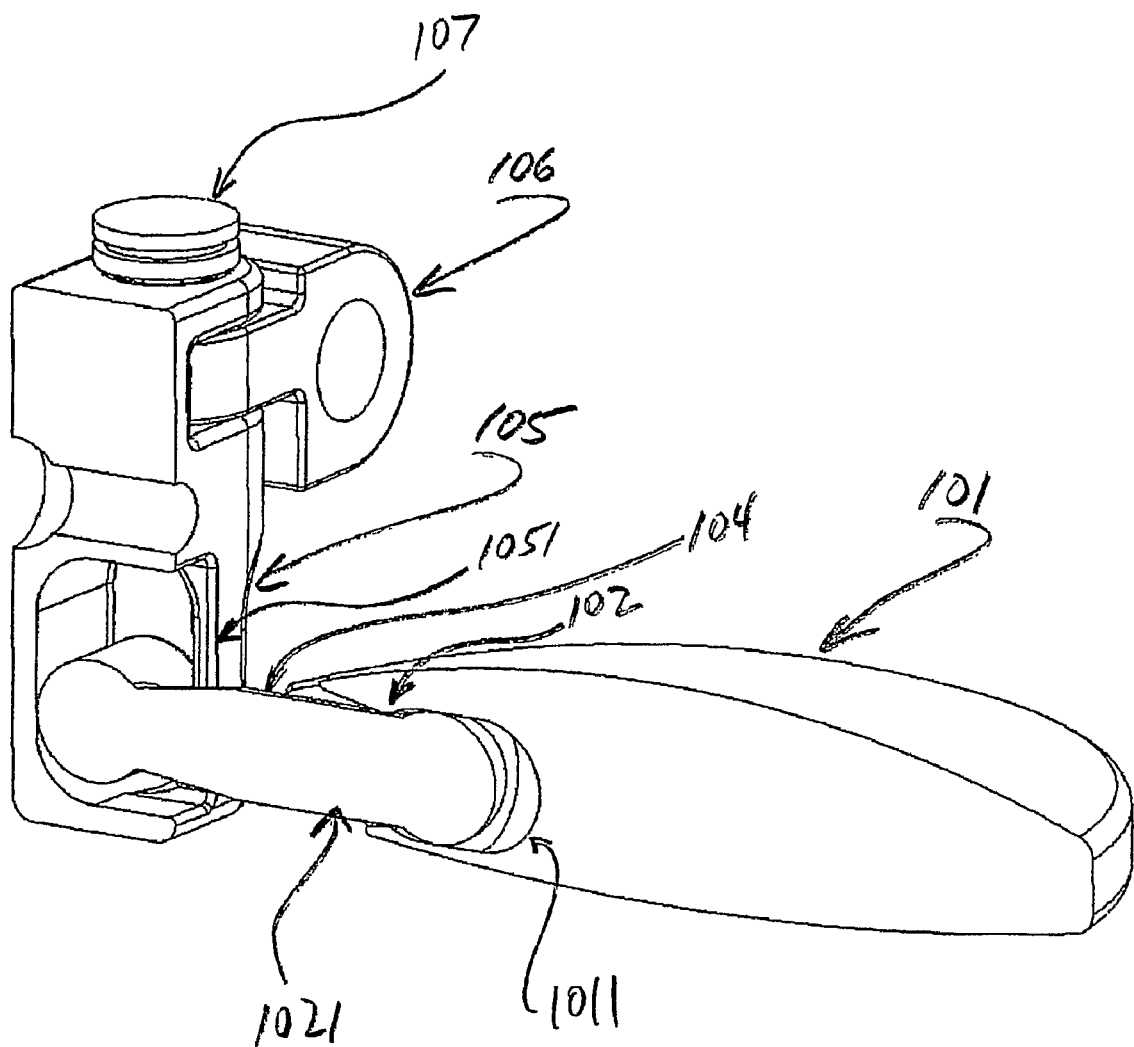
FIG. 3. Shows a side view cut-away of the invention.

The device can be divided into three distinct parts: a sliding bracket assembly, a sliding rod and an artificial disk assembly.
Artificial Disk Assembly:

The artificial disk assembly (101) consists of a central plate as a support mechanism for the upper and lower cushion plates which would be in contact with the vertebrae. The cushion plates are mated to the central plate that lies between them. Alternatively, the artificial disk can be made of one piece of material. The artificial disk is connected to the sliding rod (104) that passes through a hinge (102) and more particularly in the preferred embodiment a collar (102), and the sliding rod is inserted into the sliding bracket (105). In the preferred embodiment, the artificial disk would be solid with upper and lower convex cushion plates to complementarily fit the shape of the opposing faces of the vertebrae. The figures show a horizontal cross section of the disk in the shape of a round or elliptical disc. However the final shape would also include "kidney" shape to allow room for the spinal cord clearance. Other embodiments include folding or sliding plates on top of each other for the sake of the size and microsurgery.

In the preferred embodiment, the vertical cross section of the cushion plates shows a bulge at the middle to mimic natural spinal discs and to complementarily mate with the shape of the opposing faces of the vertebrae. The disc can be made of metal and plastic, whether titanium, stainless steel or other metal that can be left for long periods of time in the body. Plastics that can be used for the cushion include polymers like polyethylene, or any other plastic that can be left for long periods of time in the human body. The disc can be made of one material, rather than a combination. For example, if a polymer is strong enough, it may be used for the entire disk. Similarly, a ceramic disc could be used. Any appropriate shape for the disc that sufficiently mimics the shape of the natural disk may be used. The disk may be one or several parts that are attached together in combination to form the disk and the hinge.

The interior of the disk has a hollow cavity or void (1011) that extends past the entry hole (1021) along the edge in order to accommodate one end of the sliding rod. As further explained below, the shape and size of the hollow cavity determines the range of angular motion of the rod while the depth of the cavity is used to accommodate motion toward and back from the sliding bracket that is mounted to the vertebrae. In another embodiment, the sliding rod can be comprised of two telescoping sleeves so that as the disk moves back and forth, the far end of the sliding rod does not extend into the tissue behind the sliding bracket. The sliding rod (104) is attached to the disk (101) by means of a collar (102) that is shaped so that it holds the rod in place while permitting sliding and rotating motion.

The collar is any mechanical technique to limit the motion of the sliding rod positioned at the entry hole into the disk. In the preferred embodiment, it is a flared entry hole into the disk assembly. The shape of the flaring determines the range of angular movement of the rod. Practitioners of ordinary skill will recognize that other techniques may be used as a collar. For example, a simple ring around the rod provides limitations on motion depending on the relative difference between the inner diameter of the ring and the diameter of the rod. Where that difference is small, the permitted motion is limited. Other techniques include using set screws or other kinds of shapes at the entry hole into the disk that essentially perform the equivalent as the flared collar by blocking angulation of the sliding rod.

The cross section of the collar (102) is such that the minimum cross sectional diameter of the entry hole is greater than the diameter of the rod, while at the same time less than the diameter of the spherical or ovoid end of the rod that will remain embedded within the void within the disk (1011). The shape of the interior surface of the entry hole (1021) into the collar (102) is designed to limit the range of movement of the sliding rod at that point. A smaller flaring of the collar (102) opening permits less lateral angular movement of the sliding rod. A larger flaring permits more movement. In this manner, the range of lateral (i.e. in the horizontal plane) and vertical angular motion of the sliding rod (104) relative to the disk (101) can be limited within a set range determined by the geometry of the collar and the internal cavity (1011). In the preferred embodiment, the maximum lateral angular motion of the sliding rod within the hinge is less than approximately 15 degrees, and preferably no more than about 5.1 degrees. The maximum vertical angular motion is less than approximately 15 degrees and preferably no more than about 11.8 degrees. Practitioners of ordinary skill will recognize that the collar can have set screws inserted transversely to the longitudinal axis of the sliding rod and that these set screws can be adjusted to limit the permissible lateral movement.
Sliding Bracket Assembly:

The sliding bracket (105) can take different shapes depending on the location and application. Any typical attachment method to the vertebrae may be used to fixedly mount the Sliding Bracket Assembly on one of the two vertebrae neighboring the location the disc will be inserted. In one embodiment, the Sliding Bracket Assembly is a piece of metal or other appropriate solid material curved to fit the shape of the vertebrae curvature. In this embodiment, the physician has the opportunity to reshape/bend the bracket to fit the shape of the particular vertebrae being worked on. Connection to the vertebrae can be achieved by means of screws or clamps, in the latter case, which go around the vertebrae to avoid disturbing the vertebrae body.

In another embodiment, the sliding bracket assembly can be comprised of a three (3)-part folding assembly shown in the accompanying figures. Folding brackets could allow for smaller incisions (i.e. for microsurgery). In the preferred embodiment, the screw mounts (106) have pivot flanges that insert into the body of the sliding bracket (105). This is held into place by the king pins (107), which slide into the sliding bracket (105) and hold the screw mounts (106) in place. The king pin component can be fastened to the sliding bracket by screws, rivets or other methods well known in the art. In another embodiment, the screw mounts (106) share the same king pin. This form of the invention provides for a smaller space and closer spacing of the screw mounts, which is especially appropriate for smaller, cervical vertebrae. In another embodiment, the assembly can be comprised of sliding plates, sliding over each other and stored in the middle section. The sliding plates are extracted over the vertebrae body after the device is placed at its location and partially secured.

Practitioners of ordinary skill will recognize that the screw mounts (106) can be replaced with a clamping mechanism that tightens around the waist of the vertebrae. Such a strap device could either partially or wholly surround the vertebrae and then be tightened by means of screw assemblies that are fitted to the ends of the strap.

The sliding bracket (105) consists of a grooved bracket that is part of the Sliding Bracket Assembly (106) and fitted to the sliding rod (104). The groove (1051) is specially shaped so that the sliding rod can move freely within the bounds of the length of the groove. The shape of the groove (1051) in combination with the shape of the end of the sliding rod (1052) that is mounted within it permits the sliding rod to move up and down within the groove, with limits on rotational movement and lateral motion. The groove is dimensioned to establish the motion limits. This bracket could also be a folding bracket on top of others for the sake of microsurgery.

Figure 4:
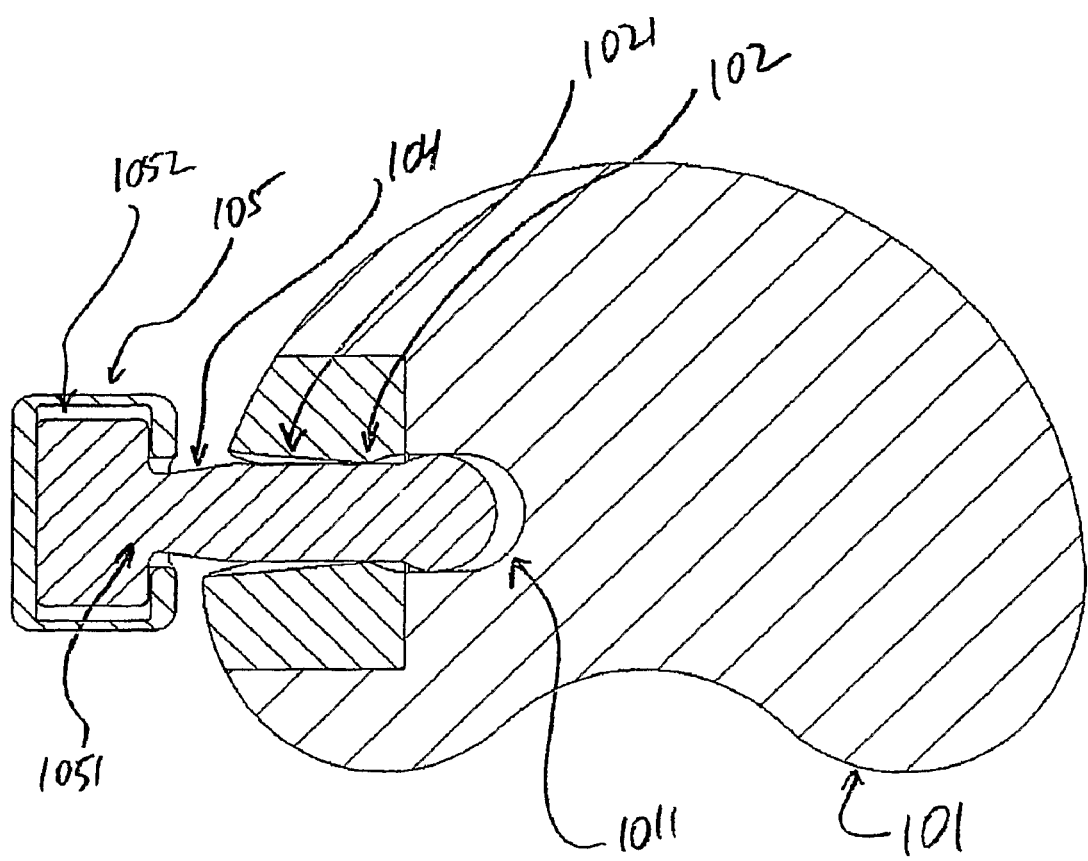
FIG. 4. Shows a cut-away top view, the cut is along the horizontal plane.
Figure 5:
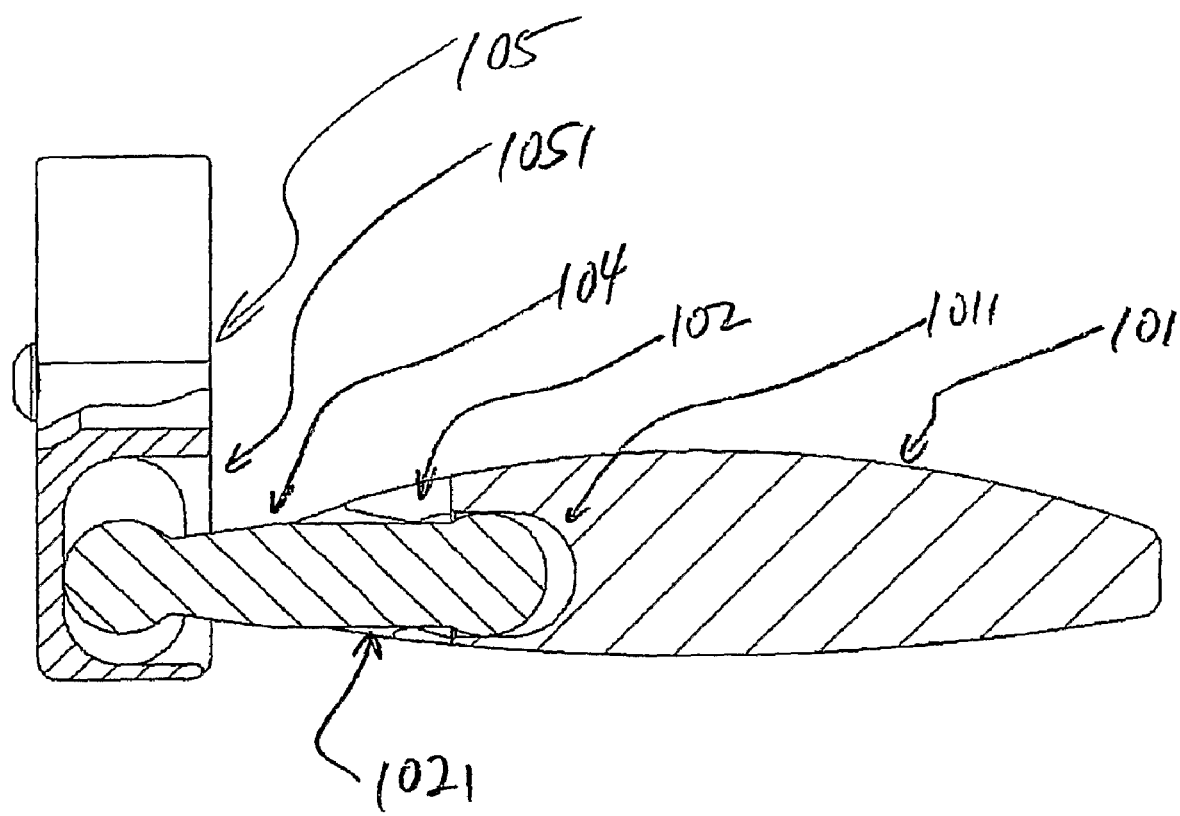
FIG. 5. Shows a cut-away side view, the cut is along the vertical plane.

FIG. 4 shows a horizontal cross section of the sliding bracket and the shape of the groove (1051). In one embodiment, the end of the sliding rod that fits in the groove is substantially spherical, whereby the diameter of the sphere is less than the widest cross section of the groove (1051) but greater than the cross section of the groove opening. In this way, the rod can move but cannot be pulled out of the groove. In another embodiment, the end of the sliding rod that fits in the groove is substantially T shaped. That is, there is a small member (1052) whose longitudinal axis that is transverse to the main longitudinal axis of the sliding rod (104). The length of the transverse member (1052) is less than the widest cross section of the groove (1051) but longer than the cross section of the groove opening. In this embodiment, the sliding rod can slide vertically as well as provide angular hinging vertically, but it does not appreciably move laterally. In this embodiment, most of the motion is set by the geometry of the disk opening (1021) as well as the shape of the collar (102). When the T shaped member (1052) rotates, the transverse length of the member and its diameter prevents it from twisting into a position where it will exit the groove (1051). This is because the diagonal distance within the solid from opposing corners of the member is greater than the width of the interior of the groove. This dimensional relationship limits the twisting of the rod itself. In addition, this relationship limits the lateral movement of the rod along the axis of the T shaped member, which is perpendicular to the longitudinal axis of the rod. This prevents the rod, and therefore the disk, from moving back and forth laterally.

Sliding Rod:

The sliding rod (104) connects the Sliding Bracket Assembly (105) to the Artificial Disk Assembly (101). The sliding rod provides means for up, down, lateral and rotational movements of the Artificial Disc Assembly. By various shapes and designs of the sliding rod, the desired disc movement and motion limit stops can be achieved. The sliding rod, in one embodiment, is a rod of metal, typically stainless steel or other surgical quality metals, plastics or other sufficiently biomaterials, with spherically shaped ends, such that the diameter of the spherical end is greater than the diameter or cross section of the rod itself. One end fits inside the groove of the sliding bracket such that it freely moves but cannot be disconnected. The other spherical end fits into the hollow cavity or void that opens along the side of the artificial disk (1011) that resides past the hinge (102). The hollow cavity (1011) is typically spherically or ovoid in shape, and its size sufficiently large that the spherical end of the sliding rod can freely move within it, but enough of the spherical shape is included, that is, the hollow cavity constitutes more than a hemisphere, so that the spherical end cannot be detached from it. Motion limits on one or both ends of the sliding rod assembly can be established by several means. The width of the opening of the groove (1051) on the surface of the sliding bracket can be set in order to limit the motion of the sliding rod. The possible range of opening widths is up to the diameter of the spherical end down to the diameter of the sliding rod. Depending on the width within this range, there will be a limited range of angular motion.

An alternative shape for one or both ends of the sliding rod is to use a "T" component rather than a spherical end. In that case, the groove in the sliding bracket will be changed to mate appropriately with the T component. This approach prevents transverse motion of the disc. In the preferred embodiment, the hinge is placed along the side of the disk such that the longitudinal axis of the sliding rod is perpendicular to the anterior-posterior axis through the vertebrae which would be a vertical line through the center of the disk in FIG. 4. As a result, the lateral movement within the groove, that is, the maximum lateral motion of the sliding rod along the longitudinal axis of the T member (1052), is limited to less than 5 millimeters and preferably about 1.25 millimeters in either direction. In this manner, the limitation of the lateral movement of the T member prevents the artificial disk from impacting the spinal chord. The T member can be used with the hinge by changing its shape so that the T fits into a mostly cylindrical cavity rather than a mostly spherical one.

Although the present invention has been described and illustrated in detail, it is to be clearly understood that the same is by way of illustration and example only, and is not to be taken by way of limitation. The described embodiments of the invention are intended to be exemplary and numerous equivalent variations and modifications will be apparent to those skilled in the art. All such variations and modifications are intended to be within the scope of the present invention as defined in the appended claims It is appreciated that various features of the invention which are, for clarity, described in the context of separate embodiments may also be provided in combination in a single embodiment. Conversely, various features of the invention which are, for brevity, described in the context of a single embodiment may also be provided separately or in any suitable combination. The spirit and scope of the present invention are to be limited only by the terms of the appended claims.

I claim:

1. An artificial spinal disk prosthesis for mounting onto a vertebrae of a patient's body using a bracket comprising in combination:
   a bracket having a groove on at least one side thereof;
   an artificial spinal disk having a hole along the side of the disk;
   a rod with a first end and second end, the first end being slidably coupled to the groove and the second end being slidably and rotatably coupled to the disk by passing through the hole along the side of the disk, whereby to permit a controlled range of motion to accommodate movement of the patient's body, wherein the disk further comprises a collar that surrounds the hole where the rod enters the disk, the collar having a cross-sectional shape perpendicular to a longitudinal axis of the rod relative to the cross-sectional shape of the rod such that the second end cannot be withdrawn through the collar while the rod can rotate within the confines of the collar.

2. The spinal disk prosthesis of claim 1, wherein the second end of the rod is substantially either spherical or ovoid in shape.

3. The spinal disk prosthesis of claim 2, wherein the disk has an interior cavity having a depth along a longitudinal axis of the rod such that a distance of travel within the cavity along a longitudinal axis of the rod is equal to or greater than zero and less than approximately 5 millimeters.

4. The spinal disk prosthesis of claim 1, wherein a lateral cross sectional shape of the collar is such that it limits lateral angular motion of the rod, as measured from the longitudinal axis of the rod to a horizontal axis passing through a center of the hole.

5. The spinal disk prosthesis of claim 1, wherein a vertical cross sectional shape of the collar is such that it limits vertical angular motion of the rod, as measured from a longitudinal axis of the rod to a horizontal axis passing through the center of the hole.

6. The spinal disk prosthesis of claim 1, wherein a width of the groove is a dimension such that a maximum range of travel of the first end of the rod within the groove in a direction both substantially perpendicular to a longitudinal axis of the sliding rod and substantially transverse to the length of the groove is equal to or less than approximately 5 millimeters.

7. The spinal disk prosthesis of claim 1, wherein a diameter of the rod is less than approximately 10 millimeters.

8. The spinal disk prosthesis of claim 1, wherein the bracket encloses the first end of the rod such that the first end does not appreciably penetrate past a back of the bracket at any point in travel of the disk along a longitudinal axis of the rod.

9. The spinal disk prosthesis of claim 1, wherein a groove width relative to a width of the first end of the rod is dimensioned such that a maximum amount of travel of the rod is less than approximately 5 millimeters along a anterior-posterior axis of the rod.

10. The spinal disk prosthesis of claim 1, wherein the hole is located at a position along a side of the disk such that a longitudinal axis of the rod is substantially perpendicular to or parallel to an anterior posterior axis of the rod.

11. The spinal disk prosthesis of claim 10, wherein the groove has a length less than approximately 10 millimeters.

12. The spinal disk prosthesis of claim 10, wherein the bracket encloses the first end such that the first end does not appreciably protrude out of a back of the bracket when the disk travels toward the bracket.

13. The spinal disk prosthesis of claim 1, wherein a groove width relative to a width of the first end of the rod and the shape of the collar are both dimensioned such that a maximum amount of travel of a disk edge immediately adjacent to a patient's spinal cord is less than approximately 5 millimeters along a anterior-posterior axis of the rod.

14. The spinal disk prosthesis of claim 1, wherein the rod is either hollow or solid.

15. The spinal disk prosthesis of claim 1, wherein the hole is located at a position along a side of the disk such that a longitudinal axis of the rod is either substantially along an anterior-posterior axis of the rod, or is between approximately zero degrees and approximately 90 degrees from an anterior-posterior axis of the rod.

16. The spinal disk prosthesis of claim 15, wherein a length of the groove is less than approximately 10 millimeters.

17. The spinal disk prosthesis of claim 15, wherein the bracket encloses the first end such that the first end does not appreciably protrude out of a back of the bracket when the disk travels toward the bracket.

18. The spinal disk prosthesis of claim 1, wherein the first end of the rod is substantially cylindrical in shape whereby said cylindrical shape has a longitudinal axis substantially perpendicular to a longitudinal axis of the rod.

19. The spinal disk prosthesis of claim 18 wherein a distance of travel of the rod in a direction transverse to a direction of the groove and along a longitudinal axis of the cylindrical shape of the first end is less than approximately 2 millimeters.

20. The spinal disk prosthesis of claim 1, wherein the rod is comprised of two sections where one section telescopes into the other when the disk moves toward the bracket.

21. The spinal disk prosthesis of claim 1, wherein the disk is further comprised of an interior cavity that receives the second end of the rod, said cavity having a dimension along a direction of the longitudinal axis of the rod such that the second end will travel within the disk along the longitudinal axis of the rod as the rod slides in and out of the disk.

22. The spinal disk prosthesis of claim 1, wherein the bracket further includes pivotally mounted screw mounts.

23. An artificial spinal disk device to be inserted between two vertebrae of a patient's body, the device being comprised of a bracket with a groove, an artificial disk, and a rod with a first end and second end, wherein the first end of the rod is slidably coupled with the groove, wherein the second end is slidably and rotatably coupled to the disk by passing through an entry hole along the side of the disk, whereby to permit controlled range of motion to accommodate movement of the patient's body, wherein the disk further comprises a collar that surrounds the hole where the rod enters the disk, the collar having a cross-sectional shape perpendicular to a longitudinal axis of the rod relative to the cross-sectional shape of the rod such that the second end cannot be withdrawn through the collar while the rod can rotate within the confines of the collar.

24. The device of claim 23, wherein the shape of the collar is such that it limits angular range of movement of the rod, as measured from a longitudinal axis of the rod to a horizontal axis passing through a center of the hole, wherein the disk is further comprised of a cavity into which the second end of the rod fits, said cavity having a dimension along the longitudinal axis of the rod such that the cavity permits the second end of the rod to travel within the cavity along the longitudinal axis of the rod, and the dimension is such that the distance of travel of the second end of the rod within the cavity preferably is less than or equal to approximately 5 millimeters.

25. The device of claim 24, wherein the shape of the collar is such that a maximum angle of a longitudinal axis of the rod to a horizontal axis of the disk is a value equal to or less than approximately 15 degrees, and/or a maximum angle of the longitudinal axis of the rod to a longitudinal axis of the entry hole is a value less than approximately 15 degrees.

26. The device of claim 24, wherein the shape of the collar is such that a maximum vertical angle of the longitudinal axis of the rod to a longitudinal axis of the entry hole is a value less than approximately 15 degrees.

27. The device of claim 24, wherein a shape of the collar is such that a maximum lateral angle of the longitudinal axis of the rod to a longitudinal axis of the entry hole is a value less than approximately 15 degrees.

28. A spinal disk prosthesis for mounting onto a vertebrae of a patient's body, comprised of:
a bracket with a groove;
a rod with a first end and a second end, the first end slidably coupled to the groove; and
an artificial disk slidably and rotatably coupled to the second end with a coupler having a hole through which the rod passes, whereby to permit a controlled range of motion to accommodate movement of the patient's body, wherein the coupler is a collar that surrounds the hole where the rod enters the disk, the collar having a cross-sectional shape perpendicular to a longitudinal axis of the rod relative to the cross-sectional shape of the rod such that the second end cannot be withdrawn through the collar while the rod can rotate within the confines of the collar.

29. The spinal disk prosthesis of claim 28, wherein the bracket further includes pivotally mounted screw mounts.

* * * * *